United States Patent [19] [11] Patent Number: 5,958,967
Jacobsen et al. [45] Date of Patent: Sep. 28, 1999

[54] CIS-3,4-CHROMAN DERIVATIVES USEFUL IN THE PREVENTION OR TREATMENT OF ESTROGEN RELATED DISEASES OR SYNDROMES

[75] Inventors: Poul Jacobsen, Slangerup; Svend Treppendahl, Virum; Paul Stanley Bury, København NV; Anders Kanstrup, Espergærde; Lise Brown Christiansen, Lyngby, all of Denmark

[73] Assignee: Novo Nordisk A/S, Bagsvaerd, Denmark

[21] Appl. No.: 08/958,060

[22] Filed: Oct. 27, 1997

Related U.S. Application Data

[60] Provisional application No. 60/031,246, Nov. 12, 1996.

[30] Foreign Application Priority Data

Oct. 28, 1996 [DK] Denmark .................. 1196/96

[51] Int. Cl.⁶ ............ A61K 31/40; C07D 405/10; C07D 405/12
[52] U.S. Cl. .............................. 514/422; 548/525
[58] Field of Search ............... 548/525; 514/422

[56] References Cited

U.S. PATENT DOCUMENTS 3,340,276  9/1967  Carney et al. ............. 260/345.2
3,535,344  10/1970  Irmscher et al. ........... 260/345.2
5,451,603  9/1995  Piggott ..................... 514/422
5,696,149  12/1997  Korsgaard et al. ......... 514/422
5,756,539  5/1998  Skrumsager et al. ....... 514/456
5,780,502  7/1998  Guldhammer ............. 514/456

FOREIGN PATENT DOCUMENTS

WO 94/20098  9/1994  WIPO .
WO 96/21444  7/1996  WIPO .

OTHER PUBLICATIONS

Salman et al., J. Med Chem., vol. 26, pp. 592–595 (1983).

*Primary Examiner*—Laura L. Stockton
*Attorney, Agent, or Firm*—Steve T. Zelson; Carol E. Rozek

[57] ABSTRACT

The present invention relates to therapeutically active compounds of formula I

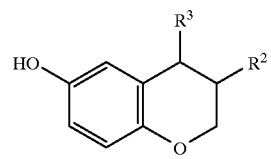

(I)

a method of preparing the same and to pharmaceutical compositions comprising the compounds. The novel compounds are useful in the prevention or treatment of estrogen related diseases or syndromes,

16 Claims, No Drawings

CIS-3,4-CHROMAN DERIVATIVES USEFUL IN THE PREVENTION OR TREATMENT OF ESTROGEN RELATED DISEASES OR SYNDROMES

CROSS-REFERENCE TO RELATED APPLICATIONS

This application claims priority under 35 U.S.C. 119 of Danish application 1196/96 filed 28 Oct. 96, and U.S. provisional patent application Ser. No. 60/031,246, filed 12 Nov. 1996, the contents of which are fully incorporated herein by reference.

FIELD OF THE INVENTION

The present invention relates to new cis-3,4-chroman derivatives and the use of such compounds in the prevention or treatment of estrogen related diseases or syndromes, preferably diseases or syndromes caused by an estrogen-deficient state in a mammal, in particular bone loss, osteoporosis, cardiovascular diseases, cognitive disorders, senile dementia-Alzheimer's type, menopausal symptoms, including flushing and urogenital atrophy, dysmenorrhea, threatened or habitual abortion, dysfunctional uterine bleeding, acne, hirsutism, prostatic carcinoma, post-partum lactation, and the use of such compounds in a contraceptive method or as an aid in ovarian development.

BACKGROUND OF THE INVENTION

The osteopenia that accompanies the menopause continues to represent a major public health problem. Left unchecked, the cumulative loss of bone can potentially compromise the skeleton's structural integrity, resulting in painful and debilitating fractures of the wrist, spine and femur. Efforts to reduce the risk and incidence of fractures have focused on the development of therapies that conserve skeletal mass by inhibiting bone resorption. Among various treatment modalities, estrogen replacement therapy remains the preferred means to prevent the development of post menopausal osteoporosis (Lindsey R, Hart D M, MacClean A 1978, "The role of estrogen/progestogen in the management of the menopause", Cooke I D, ed, Proceedings of University of Sheffield symposium on the role of estrogen and progestogen in the management of the menopause, Lancaster, UK: MTP Press Ltd. pp. 9–25; Marshall D H, Horsmann A, Nordin BEC 1977, "The prevention and management of post-menopausal osteoporosis.", Acta Obstet Gynecol Scand (Suppl) 65:49–56; Recker R R, Saville P D, Heaney R P 1977, "Effect of estrogen and calcium carbonate on bone loss in post-menopausal women", Ann Intern Med. 87:649–655; Nachtigall L E, Nachtigall R H, Nachtigall R D, Beckman E M 1979, "Estrogen replacement therapy", Obstet Gynecol. 53:277–281) and it is now accepted that estrogens significantly decrease fracture incidence and risk (Krieger N, Kelsey J L, Holford T R, O'Connor T 1982, "An epidemiological study of hip fracture in postmenopausal women", Am J Epidemiol. 116:141–148; Hutchinson T A, Polansky S M, Feinstein A R 1979, "Post-menopausal estrogens protect against fractures of hip and distal radius: A case-control study", Lancet 2:705–709; Paginini-Hill A, Ross R K, Gerkins V R, Henderson B E, Arthur M, Mack T M 1981, "Menopausal oestrogen therapy and hip fractures", Ann Intern Med. 95:28–31; Weiss N S, Ure C L, Ballard J H, Williams A R, Daling J R 1980, "Decreased risk of fractures on the hip and lower forearm with post-menopausal use of estrogen", N Eng J Med. 303:1195–1198).

While the beneficial actions of estrogen replacement therapy on the skeleton are clearly significant, there is also considerable evidence for a positive effect of estrogen on the cardiovascular system. Previous studies have attributed these actions to estrogen's effects on serum lipids, but recent data has now shown that in addition to the effects on the lipid profile, estrogen can also directly influence vessel wall compliance, reduce peripheral resistance and prevent atherosclerosis (Lobo R A 1990, "Cardiovascular implication of estrogen replacement therapy", Obstetrics and Gynaecology, 75:18S–24S; Mendelson M E, Karas R H 1994, "Estrogen and the blood vessel wall", Current Opinion in Cardiology, 1994(9):619–626). Based on available epidemiological data, the overall impact of these physiological and pharmacological actions of estrogen is an age independent reduction in cardiovascular mortality and morbidity in women (Kannel W H, Hjortland M, McNamara P M 1976 "Menopause and risk of cardiovascular disease: The Framingham Study", Ann Int Med, 85:447–552). Furthermore, a more recent analysis has concluded that post-menopausal estrogen replacement therapy reduces the risk of cardiovascular disease by approximately 50 percent (Stampfer M J, Colditz G A 1991, "Estrogen replacement therapy and coronary heart disease: a quantitative assessment of the epidemiological evidence", Preventive Medicine, 20:47–63.).

In addition to the positive effects of estrogen on bone and cardiovascular system, there are now data which indicate that the central nervous system can benefit from estrogen replacement therapy. Short term studies in human subjects have shown that increased levels of estrogen are associated with higher memory scores in post menopausal women (Kampen D L, Sherwin B B 1994, "Estrogen use and verbal memory in healthy postmenopausal women", Obstetrics and Gynecology, 83(6):979–983). Furthermore, the administration of exogenous estrogen to surgically post menopausal women specifically enhances short-term memory. Moreover, the effects of estrogen on cognition do not appear confined to short-term effects as epidemiological findings indicate that estrogen treatment significantly decreases the risk of senile dementia-Alzheimer's type in women (Paganini-Hill A, Henderson V W, 1994, "Estrogen deficiency and risk of Alzheimer's disease in women", Am J Epidemiol, 140:256–261; Ohkura T, Isse K, Akazawa K, Hamamoto M, Yoshimasa Y, Hagino N, 1995, "Long-term estrogen replacement therapy in female patients with dementia of the Alzheimer Type: 7 case reports", Dementia, 6:99–107). While the mechanism whereby estrogens enhance cognitive function is unknown, it is possible to speculate that the direct effects of estrogen on cerebral blood flow (Goldman H, Skelley Eb, Sandman C A, Kastin A J, Murphy S, 1976, "Hormones and regional brain blood flow", Pharmacol Biochem Rev. 5(suppl 1):165–169; Ohkura T, Teshima Y, Isse K, Matsuda H, Inoue T, Sakai Y, Iwasaki N, Yaoi Y, 1995, "Estrogen increases cerebral and cerebellar blood flows in postmenopausal women", Menopause: J North Am Menopause Soc. 2(1):13–18) and neuronal cell activities (Singh M, Meyer E M, Simpkins J W, 1995, "The effect of ovariectomy and estradiol replacement on brain-derived neurotrophic factor messenger ribonucleic acid expression in cortical and hippocampal brain regions of female Sprague-Dawley rats", Endocrinology, 136:2320–2324; McMillan P J, Singer C A, Dorsa D M, 1996, "The effects of ovariectomy and estrogen replacement on trkA and choline acetyltransferase mRNA expression in the basal forebrain of the adult female Sprague-Dawley rat", J Neurosci., 16(5):1860–1865) are potential effectors for these beneficial actions.

The therapeutic applications of naturally occurring estrogens and synthetic compositions demonstrating estrogenic activity alone or in combination are not limited to the chronic conditions described above. Indeed, the more traditional applications of estrogen therapies would include the following: relief of menopausal symptoms (i.e. flushing and urogenital atrophy); oral contraception; prevention of threatened or habitual abortion, relief of dysmenorrhea; relief of dysfunctional uterine bleeding; an aid in ovarian development; treatment of acne; diminution of excessive growth of body hair in women (hirsutism); treatment of prostatic carcinoma: and suppression of post-partum lactation [Goodman and Gilman, The Pharmacological Basis of Therapeutics (Seventh Edition) Macmillan Publishing Company, 1985, pages 1421–1423].

Even though the beneficial effects of estrogen replacement on a wide variety of organ systems and tissues appear indisputable, the dose and duration of estrogen therapy is also associated with an increased risk of endometrial hyperplasia and carcinoma. The use of concomitant cyclic progestins does reduce the risk of endometrial pathology, but this is achieved at the expense of the return of regular uterine bleeding, a result that is objectionable to many patients. In addition to estrogen's stimulatory effect on the endometrium, there remains considerable controversy regarding reports of an association between long-term estrogen replacement and an increased risk of breast cancer (Bergkvist L, Adami H O, Persson I, Hoover R, Schairer C, 1989, "The risk of breast cancer after estrogen and estrogen-progestin replacement", N Eng J Med, 321:293–297; Colditz G A, Hankinson S E, Hunter D J, Willett W C, Manson J E, Stampfer M J, Hennekens C, Rosner B, Speizer F E, 1995, "The use of estrogens and progestins and the risk of breast cancer in postmenopausal women", N Eng J Med, 332(24):1589–1593). Furthermore, there are other side effects of estrogen replacement which, while they may not be life threatening, contraindicate estrogen's use and reduce patient compliance.

From the foregoing discussion it would appear that the availability of therapies which could mimic the beneficial actions of estrogen on the bone, cardiovascular system, and central nervous system without the undesirable side effects on uterus and breast, would essentially provide a "safe estrogen" which could dramatically influence the number of patients that would be able to benefit from estrogen replacement therapy. Therefore, in recognition of estrogen's beneficial effects on a number of body systems and disease conditions, there is a continuing need for the development of potent estrogen agonists which can selectively target different body tissues.

DESCRIPTION OF THE INVENTION

The present invention provides compounds of the formula (I) in which substituents $R^2$ and $R^3$ are arranged in cis-configuration:

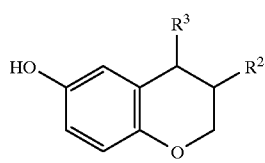

(I)

wherein:

$R^2$ is phenyl optionally substituted with 1 to 5 substituents independently selected from the group consisting of OH, halogen, nitro, cyano, SH, $SR^4$, trihalo-$C_1$–$C_6$-alkyl, $C_1$–$C_6$-alkyl, $C_1$–$C_6$-alkoxy and phenyl;

$R^3$ is:

(a) phenyl substituted with —X—$(CH_2)_n$—Y, wherein:

X is a valency bond, O or S, n is an integer in the range of 1 to 12,

Y is H, halogen, OH, $OR^4$, $NHR^4$, $NR_2^4$, $NHCOR^4$, $NHSO_2R^4$, $CONHR^4$, $CONR_2^4$, COOH, $COOR^4$, $SO_2R^4$, $SOR^4$, $SONHR^4$, $SONR_2^4$, a $C_3$–$C_7$ heterocyclic ring, saturated or unsaturated, containing one or two heteroatoms independently selected from the group consisting of O, S and N, optionally being substituted with 1 to 3 substituents independently selected from the group consisting of H, OH, halogen, nitro, cyano, SH, $SR^4$, trihalo-$C_1$–$C_6$-alkyl, $C_1$–$C_6$-alkyl and $C_1$-$C_6$-alkoxy;

(b) —$(CH_2)_n$—Y, wherein n and Y are as defined above; or (c) phenyl fused to a $C_3$–$C_7$ heterocyclic ring, saturated or unsaturated, containing one or two heteroatoms independently selected from the group consisting of O, S and N, optionally being substituted with 1 to 3 substituents independently selected from the group consisting of H, OH, halogen, nitro, cyano, SH, $SR^4$, trihalo-$C_1$–$C_6$-alkyl, $C_1$–$C_6$-alkyl and $C_1$–$C_6$-alkoxy; and $R^4$ is $C_1$–$C_6$-alkyl;

and optical and geometrical isomers, pharmaceutically acceptable esters, ethers and salts thereof.

The general chemical terms used in the above formula have their usual meanings.

For example the term $C_1$–$C_6$-alkyl includes straight-chained as well as branched alkyl groups such as methyl, ethyl, propyl, isopropyl, butyl, s-butyl and isobutyl.

The term halogen means chloro, bromo, iodo and fluoro.

The term $C_3$–$C_7$-heterocyclic ring include groups such as pyrrolidinyl, pyrrolinyl, imidazolyl, imidazolidinyl, pyrazolyl, pyrazolidinyl, pyrazolinyl, piperidyl, piperazinyl, pyrrol, 2H-pyrrol, triazolyl, pyridyl, pyrazinyl, pyrimidinyl, pyridazinyl, morpholino, thiomorpholino, isothiazolyl, isoxazolyl, oxazolyl, oxadiazolyl, thiadiazolyl and thiazolyl.

The compounds of this invention are new estrogen agonists and are useful for prevention and treatment of bone loss, prevention and treatment of osteoporosis; the prevention and treatment of cardiovascular disease; treatment and prevention of physiological disorders associated with an excess of neuropeptide Y (e.g. obesity, depression, etc.); and for regulation of glucose metabolism in e.g. non-insulin dependent diabetes melitus; and the prevention and treatment of senile dementia-Alzheimer's type in women. In addition, these estrogen agonists are useful for oral contraception; relief of menopausal symptoms (e.g. hot flushes, urogenital atrophy, depression, mania, schizophrenia, etc.); incontinence; prevention of threatened or habitual abortion; relief of dysmenorrhea; relief of dysfunctional uterine bleeding; an aid in ovarian development; treatment of acne; diminution of excessive growth of body hair is women (hirsutism); treatment of prostatic carcinoma; and the suppression of postpartum lactation. These agents also lower serum cholesterol and have a beneficial effect on plasma lipid profiles.

While the compounds of this invention are estrogen agonists in bone and cardiovascular tissues, they are also capable of acting as antiestrogens in other estrogen target organs. For example, these compounds can act as antiestrogens in breast tissue and the colon and therefore would be useful for the prevention and treatment of estrogen-dependent cancers such as breast cancers and colon cancers.

In a preferred embodiment, the present invention is concerned with cis-forms of the compounds of the following formula:

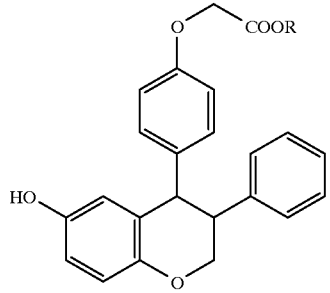

wherein R is H or $C_1$–$C_6$ alkyl.

In another preferred embodiment, the present invention is concerned with cis-forms of the compounds of the following formula:

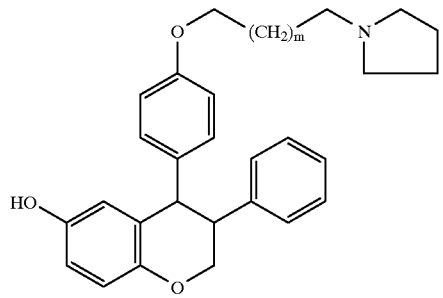

wherein m is an integer from 0 to 10.

In another preferred embodiment, the present invention is concerned with cis-forms of the compounds of the following formula:

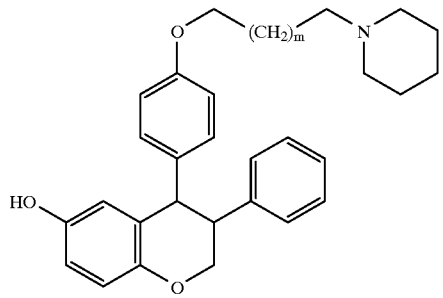

wherein m is as defined above.

In another preferred embodiment, the present invention is concerned with cis-forms of the compounds of the following formula:

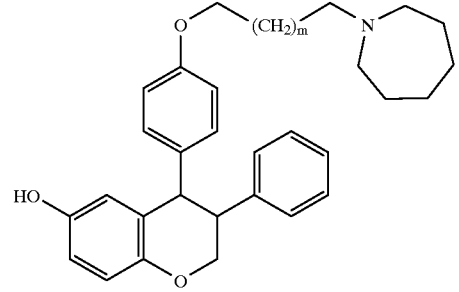

wherein m is as defined above.

In another preferred embodiment, the present invention is concerned with cis-forms of the compounds of the following formula:

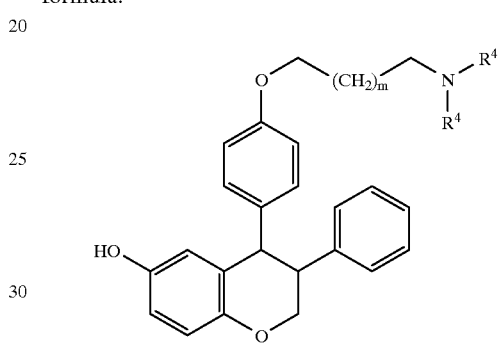

wherein m is as defined above and both $R^4$ independently are as defined above.

In another preferred embodiment, the present invention is concerned with cis-forms of the compounds of the following formula:

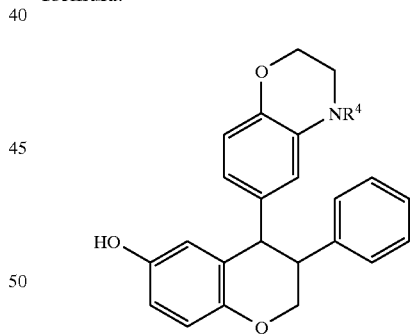

wherein $R^4$ is as defined above.

In another preferred embodiment, the present invention is concerned with cis-forms of the compounds of the following formula:

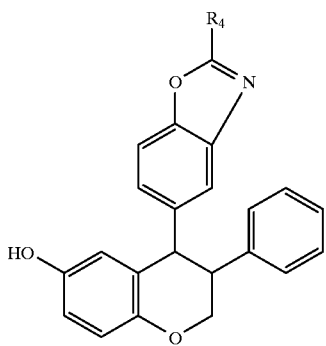

wherein $R^4$ is as defined above.

In another preferred embodiment, the present invention is concerned with cis-forms of the compounds of the following formula:

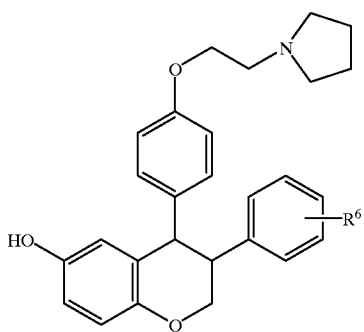

wherein $R^6$ represents one or more of the following substituents: methoxy, hydroxy, trifluormethyl, fluoro and chloro.

The most preferred compounds are the following:
(−)-cis-4-(4-(Carboxymethoxy)phenyl)-6-hydroxy-3-phenylchromane,
(−)-cis-6-Hydroxy-4-(4-(methoxycarbonylmethoxy)phenyl)-3-phenylchromane,
(−)-cis-4-(4-(Ethoxycarbonylmethoxy)phenyl)-6-hydroxy-3-phenylchromane,
(−)-cis-4-(4-(Benzyoxycarbonylmethoxy)phenyl)-6-hydroxy-3-phenylchromane,
(−)-cis-6-Hydroxy-3-phenyl-4-(4-(2-pyrrolidinoethoxy)phenyl)chromane,
(−)-cis-6-Hydroxy-3-phenyl-4-(4-(3-pyrrolidinopropoxy)phenyl)chromane,
(−)-cis-6-Hydroxy-3-phenyl-4-(4-(4-pyrrolidinobutoxy)phenyl)chromane,
(−)-cis-6-Hydroxy-3-phenyl-4-(4-(5-pyrrolidinopentoxy)phenyl)chromane,
(−)-cis-6-Hydroxy-3-phenyl-4-(4-(6-pyrrolidinohexyloxy)phenyl)chromane,
(−)-cis-6-Hydroxy-3-phenyl-4-(4-(7-pyrrolidinoheptyloxy)phenyl)chromane,
(−)-cis-6-Hydroxy-3-phenyl-4-(4-(8-pyrrolidinooctyloxy)phenyl)chromane,
(−)-cis-6-Hydroxy-3-phenyl-4-(4-(9-pyrrolidinononyloxy)phenyl)chromane,
(−)-cis-6-Hydroxy-3-phenyl-4-(4-(10-pyrrolidinodecyloxy)phenyl)chromane,
(−)-cis-6-Hydroxy-3-phenyl-4-(4-(11-pyrrolidinoundecyloxy)phenyl)chromane,
(−)-cis-6-Hydroxy-3-phenyl-4-(4-(12-pyrrolidinododecyloxy)phenyl)chromane,
(−)-cis-6-Hydroxy-3-phenyl-4-(4-(2-piperidinoethoxy)phenyl)chromane,
(−)-cis-6-Hydroxy-3-phenyl-4-(4-(3-piperidinopropoxy)phenyl)chromane,
(−)-cis-6-Hydroxy-3-phenyl-4-(4-(4-piperidinobutoxy)phenyl)chromane,
(−)-cis-6-Hydroxy-4-(4-(2-perhydroazepinoethoxy)phenyl)-3-phenylchromane,
(−)-cis-6-Hydroxy-4-(4-(3-perhydroazepinopropoxy)phenyl)-3-phenylchromane,
(−)-cis-6-Hydroxy-4-(4-(4-perhydroazepinobutoxy)phenyl)-3-phenylchromane,
(−)-cis-4-(4-(2-Dimethylaminoethoxy)phenyl)-6-hydroxy-3-phenylchromane,
(−)-cis-4-(4-(2-Diethylaminoethoxy)phenyl)-6-hydroxy-3-phenylchromane,
(−)-cis-4-(4-(2-(N-Ethyl-N-methylamino)ethoxy)phenyl)-6-hydroxy-3-phenylchromane,
(−)-cis-4-(4-(3-Dimethylaminopropoxy)phenyl)-6-hydroxy-3-phenylchromane,
(−)-cis-4-(4-(4-Dimethylaminobutoxy)phenyl)-6-hydroxy-3-phenylchromane,
(−)-cis-4-(2,3-Dihydro-1,4-benzoxazin-6-yl)-6-hydroxy-3-phenylchromane,
(−)-cis-6-Hydroxy-4-(4-methyl-2,3-dihydro-1,4-benzoxazin-6-yl)-3-phenylchromane,
(−)-cis-4-(4-Ethyl-2,3-dihydro-1,4-benzoxazin-6-yl)-6-hydroxy-3-phenylchromane,
(−)-cis-6-Hydroxy-3-(4-hydroxyphenyl)-4-(4-(2-pyrrolidinoethoxy)phenyl)chromane,
(−)-cis-6-Hydroxy-3-(4-trifluoromethylphenyl)-4-(4-(2-pyrrolidinoethoxy)phenyl)chromane,
(−)-cis-6-Hydroxy-3-(4-fluorophenyl)-4-(4-(2-pyrrolidinoethoxy)phenyl)chromane,
(−)-cis-3-(4-Chlorophenyl)-6-hydroxy-4-(4-(2-pyrrolidinoethoxy)phenyl)chromane,
(−)-cis-3-(3,4-Dimethoxyphenyl)-6-hydroxy-4-(4-(2-pyrrolidinoethoxy)phenyl)chromane,
(−)-cis-6-Hydroxy-3-(pentafluorophenyl)-4-(4-(2-pyrrolidinoethoxy)phenyl)chromane,
(+)-cis-4-(4-(Carboxymethoxy)phenyl)-6-hydroxy-3-phenylchromane,
(+)-cis-6-Hydroxy-4-(4-(methoxycarbonylmethoxy)phenyl)-3-phenylchromane,
(+)-cis-4-(4-(Ethoxycarbonylmethoxy)phenyl)-6-hydroxy-3-phenylchromane,
(+)-cis-4-(4-(Benzyloxycarbonylmethoxy)phenyl)-6-hydroxy-3-phenylchromane,
(+)-cis-6-Hydroxy-3-phenyl-4-(4-(2-pyrrolidinoethoxy)phenyl)chromane,
(+)-cis-6-Hydroxy-3-phenyl-4-(4-(3-pyrrolidinopropoxy)phenyl)chromane,
(+)-cis-6-Hydroxy-3-phenyl-4-(4-(4-pyrrolidinobutoxy)phenyl)chromane,
(+)-cis-6-Hydroxy-3-phenyl-4-(4-(5-pyrrolidinopentoxy)phenyl)chromane,
(+)-cis-6-Hydroxy-3-phenyl-4-(4-(6-pyrrolidinohexyloxy)phenyl)chromane,
(+)-cis-6-Hydroxy-3-phenyl-4-(4-(7-pyrrolidinoheptyloxy)phenyl)chromane,
(+)-cis-6-Hydroxy-3-phenyl-4-(4-(8-pyrrolidinooctyloxy)phenyl)chromane,
(+)-cis-6-Hydroxy-3-phenyl-4-(4-(9-pyrrolidinononyloxy)phenyl)chromane,
(+)-cis-6-Hydroxy-3-phenyl-4-(4-(10-pyrrolidinodecyloxy)phenyl)chromane,
(+)-cis-6-Hydroxy-3-phenyl-4-(4-(11-pyrrolidinoundecyloxy)phenyl)chromane, (+)-cis-6-Hydroxy-3-phenyl-4-(4-(12-pyrrolidinododecyloxy)phenyl)chromane,
(+)-cis-6-Hydroxy-3-phenyl-4-(4-(2-piperidinoethoxy)phenyl)chromane,
(+)-cis-6-Hydroxy-3-phenyl-4-(4-(3-piperidinopropoxy)phenyl)chromane,
(+)-cis-6-Hydroxy-3-phenyl-4-(4-(4-piperidinobutoxy)phenyl)chromane,
(+)-cis-6-Hydroxy-4-(4-(2-perhydroazepinoethoxy)phenyl)-3-phenylchromane,
(+)-cis-6-Hydroxy-4-(4-(3-perhydroazepinopropoxy)phenyl)-3-phenylchromane,
(+)-cis-6-Hydroxy-4-(4-(4-perhydroazepinobutoxy)phenyl)-3-phenylchromane,
(+)-cis-4-(4-(2-Dimethylaminoethoxy)phenyl)-6-hydroxy-3-phenylchromane,
(+)-cis-4-(4-(2-Diethylaminoethoxy)phenyl)-6-hydroxy-3-phenylchromane,
(+)-cis-4-(4-(2-(N-Ethyl-N-methylamino)ethoxy)phenyl)-6-hydroxy-3-phenylchromane,
(+)-cis-4-(4-(3-Dimethylaminopropoxy)phenyl)-6-hydroxy-3-phenylchromane,
(+)-cis-4-(4-(4-Dimethylaminobutoxy)phenyl)-6-hydroxy-3-phenylchromane,
(+)-cis-4-(2,3-Dihydro-1,4-benzoxazin-6-yl)-6-hydroxy-3-phenylchromane,
(+)-cis-6-Hydroxy-4-(4-methyl-2,3-dihydro-1,4-benzoxazin-6-yl)-3-phenylchromane,
(+)-cis-4-(4-Ethyl-2,3-dihydro-1,4-benzoxazin-6-yl)-6-hydroxy-3-phenylchromane,
(+)-cis-6-Hydroxy-3-(4-hydroxyphenyl)-4-(4-(2-pyrrolidinoethoxy)phenyl)chromane,
(+)-cis-6-Hydroxy-3-(4-trifluoromethylphenyl)-4-(4-(2-pyrrolidinoethoxy)phenyl)chromane,
(+)-cis-6-Hydroxy-3-(4-fluorophenyl)-4-(4-(2-pyrrolidinoethoxy)phenyl)chromane,
(+)-cis-3-(4-Chlorophenyl)-6-hydroxy-4-(4-(2-pyrrolidinoethoxy)phenyl)chromane,
(+)-cis-3-(3,4-Dimethoxyphenyl)-6-hydroxy-4-(4-(2-pyrrolidinoethoxy)phenyl)chromane,
(+)-cis-6-Hydroxy-3-(pentafluorophenyl)-4-(4-(2-pyrrolidinoethoxy)phenyl)chromane, and any mixture thereof including racemic mixtures.

The following compounds also form part of the disclosure of the present invention:
(±)-cis-6-Hydroxy-3-phenyl-4-(4-(2-pyrrolidinoethoxy)phenyl)-chromane,
(±)-cis-6-Hydroxy-3-(3-hydroxyphenyl)-4-(4-(2-pyrrolidinoethoxy)phenyl)chromane, including the pure enantiomers thereof.

The compounds of the invention may be prepared by resorting to the chroman chemistry which is well-known in the art, for example in P. K. Arora, P. L. Kole and S. Ray, Indian J. Chem. 20 B. 41–5, 1981; S. Ray, P. K. Grover and N. Anand, Indian J. Chem. 9, 727–8, 1971; S. Ray, P. K. Grover, V. P. Kamboj, S. B. Betty, A. B. Kar and N. Anand, J. Med. Chem. 19, 276–9, 1976; Md. Salman, S. Ray, A. K. Agarwal, S. Durani, B. S. Betty, V. P. Kamboj and N. Anand, J. Med. Chem. 26, 592–5, 1983; Teo, C., Sim, K., Bull. Singapore Natl. Inst. Chem. 22, 69–74, 1994.

However, the invention is furthermore concerned with a general method for the preparation of compounds of formula (I) comprising the steps of:

a) reacting a compound of the formula (II)

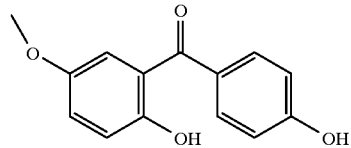

(II)

with a compound of the formula (III)

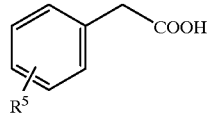

(III)

wherein $R^5$ represents 1 to 3 substituents independently selected from the group consisting of H, OH, halogen, nitro, cyano, SH, $SR^4$, trihalo-$C_1$–$C_6$-alkyl, $C_1$-$C_6$-alkyl and $C_1$–$C_6$-alkoxy, and $R^4$ is as defined above, in the presence of triethylamine and acetic anhydride to form a compound of the formula (IV)

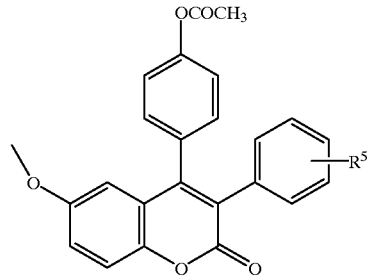

(IV)

wherein $R^5$ is as defined above, b) reducing a compound of the formula (IV) with a suitable hydride reducing agent to form a compound of formula (V)

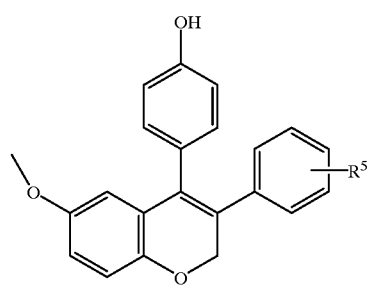

(V)

wherein $R^5$ is as defined above, c) hydrogenating a compound of the formula (V) in the presence of a suitable catalyst to form a compound of the formula (VI) with a 3,4-cis configuration

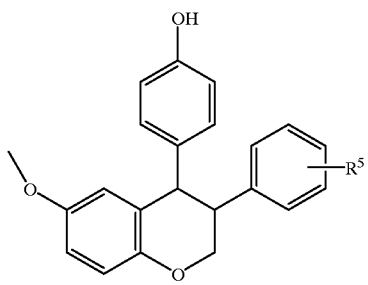

(VI)

wherein R⁵ is as defined above, d) alkylating a compound of the formula (VI) with an appropriate electrophile to form a compound of the formula (VII)

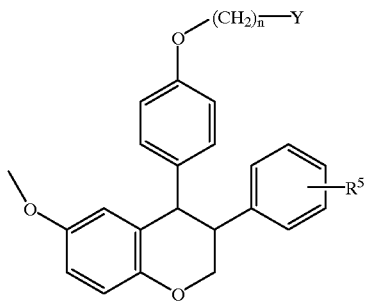

(VII)

wherein n, R⁵ and Y are as defined above, e) deprotecting a compound of formula (VII) with a suitable deprotection agent, preferably by pyridine hydrochloride fusion, to form a compound of the formula (I); or
f) nitrating a compound of the formula (VI) with a suitable nitration agent to form a compound of the formula (VIII)

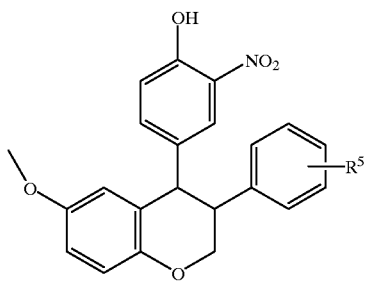

(VIII)

wherein R⁵ is as defined above, g) reducing a compound of the formula (VIII) with a suitable reducing agent, preferably by catalytic hydrogenation, to form a compound of the formula (IX)

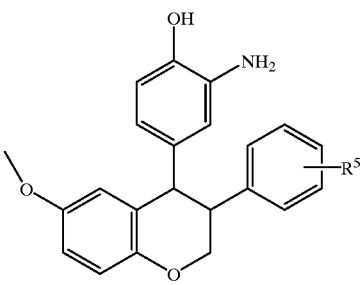

(IX)

wherein R⁵ is as defined above, h) cyclizing a compound of formula (IX) with an appropriate agent to form a compound of the formula (X) or (XI)

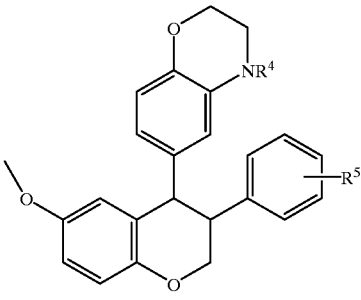

(X)

or

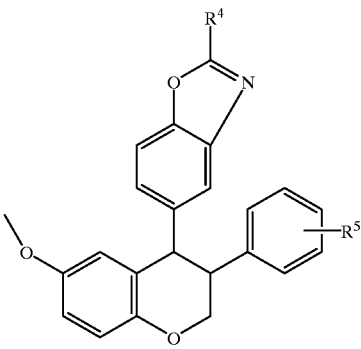

(XI)

wherein R⁴ and R⁵ are as defined above, i) deprotecting a compound of the formula (X) or (XI) with a suitable deprotection agent, preferably by pyridine hydrochloride fusion, to form a compound of the formula (I); or
j) reacting a compound of formula (VI) with trifluoromethane sulphonic acid anhydride to form a compound of the formula (XII)

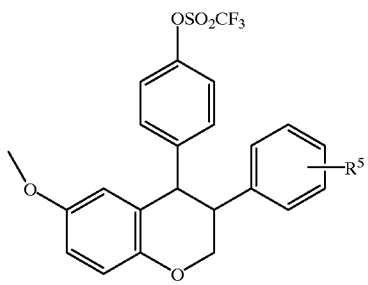

(XII)

wherein R⁵ is as defined above, k) cross-coupling a compound of the formula (XII) with the appropriate cross-coupling partner to form a compound of the formula (XIII)

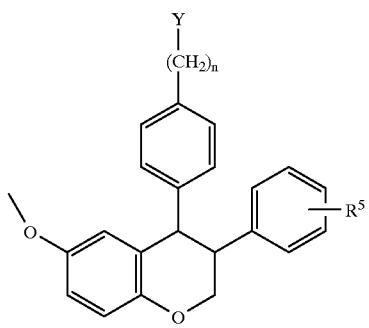

(XIII)

wherein n, $R^5$ and Y are as defined above, l) deprotecting a compound of the formula (XIII) with a suitable deprotection agent, preferably by pyridine hydrochloride fusion, to form a compound of the formula (I); or m) cyclizing a compound of the formula (XIV)

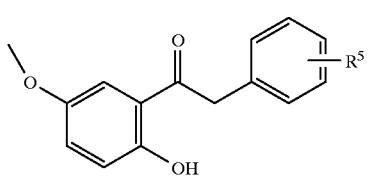

(XIV)

wherein $R^5$ is as defined above,
with paraformaldehyde in the presence of dimethylamine to form a compound of the formula (XV)

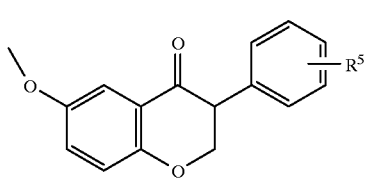

(XV)

wherein $R^5$ is as defined above, n) hydrogenating a compound of the formula (XV) in the presence of a suitable catalyst to form a compound of the formula (XVI) with a 3,4-cis configuration

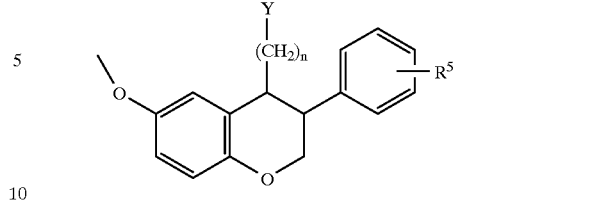

(XVI)

wherein n, $R^5$ and Y are as defined above, o) deprotecting a compound of formula (XVI) with a suitable deprotection agent, preferably by pyridine hydrochloride fusion, to form a compound of the general formula (I), p) reacting a compound of the formula (VI) with methanesulfonylchloride to form a compound of the formula (XVII)

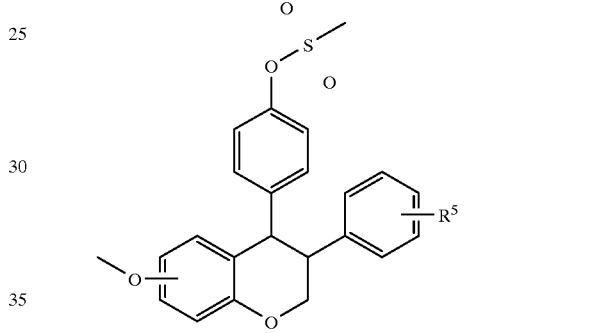

(XVII)

wherein $R^5$ is defined as above, q) deprotecting a compound of the formula (XVII) with a suitable deprotection agent, such as pyridine hydrochloride fusion or boron tribromide, to form a compound of the formula (XVIII)

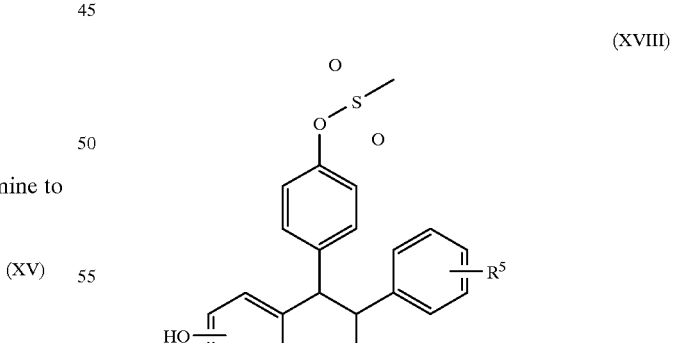

(XVIII)

wherein $R^5$ is defined as above, r) reacting a compound of the formula (XVIII) with a suitable protection agent, such as benzyl bromide or 4-methoxybenzyl bromide, to form a compound of formula (XIX)

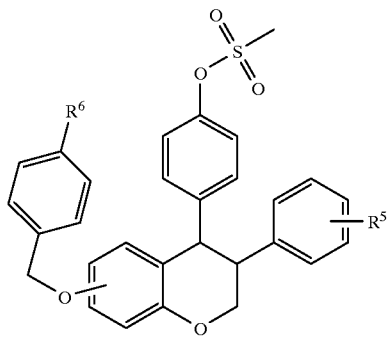
(XIX)

wherein R$^5$ is defined as above, and R$^6$ is H or methoxy, s) deprotecting a compound of the formula (XIX) with a suitable deprotection agent, such as sodium or potassium hydroxide in alcohol, to form a compound of formula (XX)

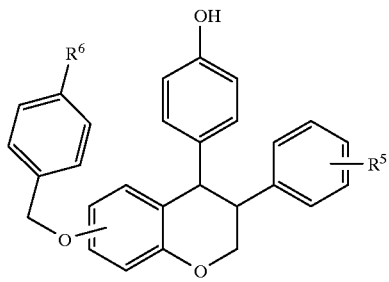
(XX)

wherein R$^5$ is defined as above, and R$^6$ is H or methoxy, t) alkylating a compound of the formula (XX) with an appropriate electrophile to form a compound of the formula (XXI)

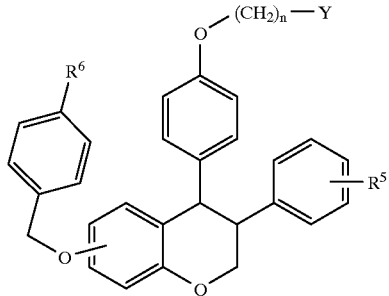
(XXI)

wherein n, R$^5$ and Y is defined as above, and R$^6$ is H or methoxy, u) deprotecting a compound of the formula (XXI) with a suitable deprotection agent, preferably catalytic hydrogenation for R$^6$ equals H or a strong acid for R$^6$ equals methoxy, to form a compound of the formula (XXII)

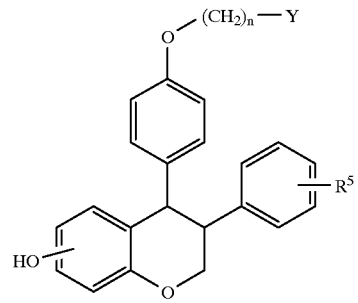
(XXII)

wherein n, R$^5$ and Y is defined as above, v) Alkylating a compound of the formula (XX) with an appropriate dihalogenated alkane such as 1,2-dibromoethane, 1-bromo-2-chloroethane, 1,4-dibromobutane, 1,6-dibromohexane, 1,8-dibromooctane, 1,10-dibromodecane, preferably catalysed by potassium iodide, to form a compound of the formula (XXIII)

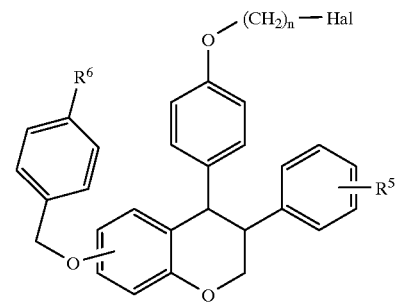
(XXIII)

wherein n and R$^5$ is defined as above, R$^6$ is H or methoxy, and Hal is chloro, bromo, or iodo, x) reacting a compound of the formula (XXIII) with an appropriate nucleophile, preferably an amine, to form a compound of the formula (XXIV)

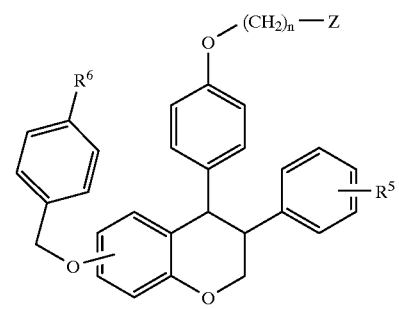
(XXIV)

wherein R$^6$ is H or methoxy, and Z is NHR$^4$, NR$_2^4$, or a C$_3$–C$_7$ heterocyclic amine optionally containing oxygen or nitrogen, optionally being substituted with 1 to 3 substituents independently selected from the group consisting of H, OH, halogen, nitro, cyano, trihalo-C$_1$–C$_6$-alkyl, C$_1$–C$_6$-alkyl and C$_1$–C$_6$-alkoxy, and n, R$^4$, and R$^5$ is defined as above, y) deprotecting a compound of the formula (XXIV) with a suitable deprotection agent, preferably catalytic hydrogenation for R$^6$ equals H or a strong acid for R$^6$ equals methoxy, to form a compound of the formula (XXV)

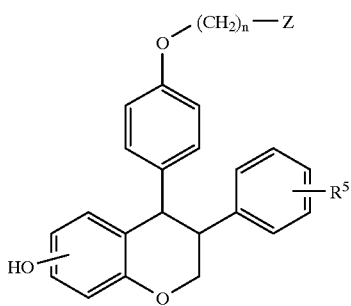

(XXV)

wherein $R^6$ is H or methoxy, and Z is $NHR^4$, $NR_2^4$, or a $C_3$–$C_7$ heterocyclic amine optionally containing oxygen or nitrogen, optionally being substituted with 1 to 3 substituents independently selected from the group consisting of H, OH, halogen, nitro, cyano, trihalo-$C_1$–$C_6$-alkyl, $C_1$–$C_6$-alkyl and $C_1$–$C_6$-alkoxy, and n, $R^4$ and $R^5$ is defined as above.

The starting benzophenones of the formula (II) are easily prepared via Friedel-Craft acylation of the appropriate dimethyl ether with p-hydroxybenzoic acid followed by selective monodemethylation with hydrobromic acid in acetic acid.

The starting deoxybenzoins of the formula (XIV) are easily prepared via the Hoesch reaction of the appropriate dimethyl ether and the appropriate substituted phenyl acetic acid derivative followed by selective monodemethylation by hydrobromic acid in acetic acid.

Optical pure compounds of formula (I) can be obtained by introducing in the above method a resolution step. The resolution can be carried out after any step of the process which results in a racemic mixture of enantiomers. Any resolution technique may be used to separate a (–)-enantiomer and/or a (+)-enantiomer from a racemic mixture, including diastereomeric salt formation and chiral HPLC.

The expression "appropriate electrophile" typically means an alkylhalogenide of the formula Y-($CH_2$ )n-Hlg, wherein Y is as defined above and Hlg is Cl, Br or I.

The cyclization step of the above method can be performed with for example a suitable activated carboxylic acid derivative followed by dehydration.

The expression "appropriate cross-coupling partner" typically means an organometallic reagent together with a transition metal catalyst, for example a Grignard reagent with a Ni(O) catalyst.

The expression "appropriate Grignard reagent" typically means an organometallic compound of the formula M-($CH_2$)-Y, wherein M is MgHlg, Hlg is Cl, Br or I and Y is as defined above.

The present invention also relates to pharmaceutical compositions comprising an effective amount of a compound according to the invention and a pharmaceutical carrier or diluent. Such compositions are preferably in the form of an oral dosage unit or parenteral dosage unit.

Furthermore, the invention is concerned with a method of treating or preventing estrogen related diseases or syndromes, preferably diseases or syndromes caused by an estrogen-deficient state in a mammal, comprising administering to a subject in need thereof an effective amount of a compound according to the invention.

The compounds of this invention are new estrogen agonists and are useful for prevention and treatment of bone loss, prevention and treatment of osteoporosis; the prevention and treatment of cardiovascular disease; treatment and prevention of physiological disorders associated with an excess of neuropeptide Y (e.g. obesity, depression, etc.); and for regulation of glucose metabolism in e.g. non-insulin dependent diabetes melitus; and the prevention and treatment of senile dementia-Alzheimer's type in women. In addition, these estrogen agonists are useful for oral contraception; relief of menopausal symptoms (e.g. hot flushes, urogenital atrophy, depression, mania, schizophrenia, etc.); incontinence; prevention of threatened or habitual abortion; relief of dysmenorrhea; relief of dysfunctional uterine bleeding; an aid in ovarian development; treatment of acne; diminution of excessive growth of body hair is women (hirsutism); treatment of prostatic carcinoma; and the suppression of postpartum lactation. These agents also lower serum cholesterol and have a beneficial effect on plasma lipid profiles.

While the compounds of this invention are estrogen agonists in bone and cardiovascular tissues, they are also capable of acting as antiestrogens in other estrogen target organs. For example, these compounds can act as antiestrogens in breast tissue and the colon and therefore would be useful for the prevention and treatment of estrogen-dependent cancers such as breast cancers and colon cancers.

In vitro estrogen receptor binding assay

An in vitro receptor binding assay was used to determine the estrogen receptor binding affinity of the compounds of this invention. This assay measures the ability of the compounds of this invention to displace $^3$H-17β-estradiol (17β-E2), from estrogen receptor (ER) obtained from rabbit uterus. Experimentally, the ER rich cytosol from rabbit uterine tissue is diluted with ER poor cytosol isolated from rabbit muscle to achieve approximately 20–25% maximal binding of 0.5 nM $^3$H-17β-E2. For each assay, fresh aliquots of cytosol are thawed on the day of analysis and diluted with assay buffer to ca. 3 mg cytosol protein/ml. The assay buffer (PB) is as follows: 10 mM $K_2HPO_4$/$KH_2PO_4$, 1.5 mM $K_2EDTA$, 10 mM monothioglycerol, 10 mM $Na_2MoO_4 \cdot 2H_2O$, 10% glycerol (v/v); pH 7.5. Radio-inert 17β-E2 is obtained from Sigma.

Test solutions are prepared in appropriate solvents (ethanol or DMSO) at a concentration of 8×10-3M and serial dilutions prepared with PB or DMSO. Aliquots of 10 μl are incubated in duplicate for each concentration tested in microtitre plates to which have been added 20 μl $^3$H-17β-E2 (assay concentration equals 0.4 nM) and 50 μl cytosol. For control samples as well as maximal binding sample, 10 μl PB is added in lieu of test compound.

Following an 18–20 hr incubation at 4° C. the reaction is terminated with 100 μl DCC slurry [0.5% activated charcoal (Sigma) and 0.005% Dextran T70 (Pharmacia) in PB] added to each sample and incubated with continuous shaking for 15 min at 4° C. DCC background counts are assessed using 50 μl of 0.3% BSA in PB in lieu of cytosol.

To separate bound and free $^3$H-17β-E2, Titertek plates are centrifuged for 10 min (800×g) at 4° C. and aliquots of 100 μl are removed from each sample for scintillation counting using Optiflour scintillation liquid. Standard and control samples are incubated in quadruplicate, while test compounds are incubated in duplicate. The mean counts per minute (cpm) in each sample is calculated, background (DCC) is subtracted, and the percent of maximal 3H-17β-E2 binding is determined. Individual cpm's are plotted against their respective concentrations of test compound (logarithmic scale), and the IC50 expressed as the compound concentration required to displace 50% of the maximal binding.

Bone Mineral Density

Bone mineral density (BMD) as a measure of bone mineral content (BMC) accounts for greater than 80% of a bone's strength. The loss of BMD with ageing and the accelerated loss following the menopause reduce the strength of the skeleton and render specific sites more susceptible to fracture; i.e. most notably the spine, wrist and hip. True bone density can be measured gravimetrically using Archimede's Principle (an invasive technique). The BMD can also be measured non-invasively using dual energy x-ray absorptiometry (DEXA). In our laboratory, we have utilized a gravimetric method to evaluate changes in BMD due to estrogen deficiency in ovariectomized rodents. Following ovariectomy (the surgical removal of the ovaries), the animals are treated with vehicle, 17β-E2 as a positive control, and/or other estrogen agonists. The objective of these investigations is to evaluate the ability of the compounds of this invention to prevent bone loss in rodent models of human disease.

Female Sprague-Dawley rats (ca. 3 to 5 months old), or female Swiss-Webster mice (ca. 3 to 5 months old) underwent bilateral ovariectomy or sham surgery. Following recovery from anesthesia the animals are randomized to the following groups, minimum of 8 animals per group:

sham animals treated with vehicle;

ovariectomized animals treated with vehicle;

ovariectomized animals treated with 25 µg estradiol/kg; and ovariectomized animals treated with 200 µg/kg of test compound.

All compounds are weighed and dissolved in vehicle solvent in sterile saline and the animals are treated daily via subcutaneous injections for 35 days. At the conclusion of the 35 day protocol, the animals are sacrificed and the femora are excised and cleaned of adherent soft tissue. In rats, the distal 1 cm of the defleshed femora are removed with a diamond wheel cut-off saw and fixed in 70% ethyl alcohol (in mice the distal 0.5 cm are removed and fixed). Following fixation in 70% ethyl alcohol (EtOH) an automated tissue processor was used to dehydrate the bone specimens in an ascending series of alcohol to 100%. The dehydration program was followed by defatting in chloroform and rehydration in distilled water. All automated tissue processing occurred under vacuum. The hydrated bones were weighed in air and weighed while suspended in water on a Mettler balance equipped with a density measurement kit. The weight of each sample in air is divided by the difference between the air weight and the weight in water to determine total bone density; i.e. organic matrix plus mineral per unit volume of tissue. After the determination of total bone density the samples are ashed overnight in a muffle furnace at 600° C. The mineral density can then be determined by dividing the ash weight of each sample by the tissue volume (i.e. air weight—weight suspended in water). The mean bone densities (total and mineral bone densities) are calculated for each group and statistical differences from the vehicle-treated and estrogen-treated controls are determined using computerized statistical programs.

Cholesterol lowering activity

The effects of the compounds of the present invention on the serum levels of total cholesterol were measured either in blood samples taken from the animals in the bone density studies described above or from ovariectomized female rats or mice that had been treated with compound for a period of not less than 28 days. In each type of experiment, blood from treated animals was collected via cardiac puncture and placed in a tube containing 30 µl of 5% EDTA/1 ml of blood. Following centrifugation at 2500 rpm for 10 minutes at 20° C. the plasma was removed and stored at −20° C. until assayed. Cholesterol was measured using a standard enzymatic determination kit purchased from Sigma Diagnostics (Kit No. 352).

Pharmaceutical preparations

The compounds of the invention, together with a conventional adjuvant, carrier or diluent, and if desired in the form of a pharmaceutically acceptable acid addition salt thereof, may be placed into the form of pharmaceutical compositions and unit dosages thereof, and in such form may be employed as solids, such as tablets or filled capsules, or liquids, such as solutions, suspensions, emulsions, elixirs, or capsules filled with the same, all for oral use; in the form of suppositories for rectal administration; or in the form of sterile injectable solutions for parenteral use (including subcutaneous administration and infusion). Such pharmaceutical compositions and unit dosage forms thereof may comprise conventional ingredients in conventional proportions, with or without additional active compounds or principles, and such unit dosage forms may contain any suitable effective amount of a compound of the invention commensurate with the intended daily dosage range to be employed. Tablets containing ten (10) milligrams of active ingredient or, more broadly, ten (10) to hundred (100) milligrams, per tablet, are accordingly suitable representative unit dosage forms.

The compounds of this invention can thus be used for the formulation of pharmaceutical preparation, e.g. for oral and parenteral administration to mammals including humans, in accordance with conventional methods of galenic pharmacy.

Conventional excipients are such pharmaceutically acceptable organic or inorganic carrier substances suitable for parenteral or enteral application which do not deleteriously react with the active compounds.

Examples of such carriers are water, salt solutions, alcohols, polyethylene glycols, polyhydroxyethoxylated castor oil, gelatine, lactose amylose, magnesium stearate, talc, silicic acid, fatty acid monoglycerides and diglycerides, pentaerythritol fatty acid esters, hydroxymethylcellulose and polyvinylpyrrolidone.

The pharmaceutical preparations can be sterilized and mixed, if desired, with auxiliary agents, emulsifiers, salt for influencing osmotic pressure, buffers and/or colouring substances and the like, which do not deleteriously react with the active compounds.

For parenteral application, particularly suitable are injectable solutions or suspensions, preferably aqueous solutions with the active compound dissolved in polyhydroxylated castor oil.

Ampoules are convenient unit dosage forms.

Tablets, dragees, or capsules having talc and/or carbohydrate carrier or binder or the like, the carrier preferably being lactose and/or corn starch and/or potato starch, are particularly suitable for oral application. A syrup, elixir or the like can be used in cases where a sweetened vehicle can be employed.

Generally, the compounds of this invention are dispensed in unit form comprising 0.05–100 mg in a pharmaceutically acceptable carrier per unit dosage.

The dosage of the compounds according to this invention is 0.1–300 mg/day, preferably 10–100 mg/day, when administered to patients, e.g. humans, as a drug.

A typical tablet which may be prepared by conventional tabletting techniques contains:

| | |
|---|---|
| Active compound | 5.0 mg |
| Lactosum | 67.0 mg Ph.Eur. |
| Avicel ™ | 31.4 mg |

| | |
|---|---|
| Amberlite ™IRP 88 | 1.0 mg |
| Magnesii stearas | 0.25 mg Ph.Eur. |

The compounds of the invention may be administered to a subject, e.g., a living animal body, including a human, in need of a compound of the invention, and if desired in the form of a pharmaceutically acceptable acid addition salt thereof (such as the hydrobromide, hydrochloride, or sulphate, in any event prepared in the usual or conventional manner, e.g., evaporation to dryness of the free base in solution together with the acid), ordinarily concurrently, simultaneously, or together with a pharmaceutically acceptable carrier or diluent, especially and preferably in the form of a pharmaceutical composition thereof, whether by oral, rectal, or parenteral (including subcutaneous) route, in an amount which is effective for the treatment of the disease. Suitable dosage ranges are 1–200 milligrams daily, 10–100 milligrams daily, and especially 30–70 milligrams daily, depending as usual upon the exact mode of administration, form in which administered, the indication toward which the administration is directed, the subject involved and the body weight of the subject involved, and the preference and experience of the physician or veterinarian in charge.

EXAMPLE 1

(±)-cis-6-Hydroxy-3-phenyl-4-(4-(2-pyrrolidinoethoxy)phenyl)-chromane

Step 1:

(4-Benzyloxyphenyl)-(2,5-dimethoxyphenyl)-methanone

Butyllithium (2.0M in hexanes, 6.6 ml, 13.2 mmol) was added dropwise under nitrogen, at −78° C. to a stirred tetrahydrofuran (20 ml) solution of 4-benzyloxy-bromobenzene (3.15 g, 11.97 mmol) to give a yellow coloured suspension, which was stirred for 10 minutes. A tetrahydrofuran (10 ml) solution of N,N-dimethyl 2,5-dimethoxybenzamide (2.09 g, 9.99 mmol) was then added slowly, and the resulting mixture warmed to room temperature over 20 h. The mixture was diluted with 50ml of 1M hydrochloric acid and the product extracted into dichloromethane (4×50 ml). The combined extracts were washed with brine, dried over sodium sulfate and evaporated to a yellow coloured solid. This crude product was purified by column chromatography on silica gel 60, using 4:1 petrol/ethyl acetate as the eluent. This gave the product as a colourless solid, which was recrystallised from hot ethanol (25 ml) to give the product as colourless platelets which were vacuum dried.

Yield 1.61 g (46%) of (4-benzyloxyphenyl)-(2,5-dimethoxyphenyl)-methanone. M.p. 111–113° C. (ethanol). $^1$H-NMR (CDCl$_3$, 300 MHz) δ: 3.70 (s, 3H), 3.78 (s, 3H), 5.13 (s, 2H), 6.85–7.02 (m, 5H), 7.30–7.47 (m, 5H), 7.82 (dm, 2H). LRMS (El) 348 (M$^+$), 257, 91.

Step 2:

(2-Hydroxy-5-methoxyphenyl)-(4-hydroxyphenyl)-methanone

Palladium on carbon catalyst (10%, 1.0 g, 0.94 mmol) was added to a stirred ethanol (500 ml) solution of (4-benzyloxyphenyl)-(2,5-dimethoxyphenyl)-methanone (10.86 g, 31.2 mmol) and the suspension hydrogenated for 18 h. The catalyst was removed by filtration, and the solvent evaporated to give an orange coloured gum. This was dissolved in glacial acetic acid (16 ml), hydrogen bromide (33% w/w in acetic acid, 8.20 ml, 46.76 mmol) added, and the resulting mixture heated to 70° C. for 18 h. The mixture was diluted with water (25 ml) and the product extracted into ethyl acetate (3×25 ml). The combined extracts were washed with brine, dried over magnesium sulfate and evaporated to a yellow gum, which was purified by column chromatography on silica gel 60, with 7:3 petrol/ethyl acetate as eluent. This gave a yellow gum, which was dissolved in a minimum of ether and precipitated by adding petrol, to give the title product as a yellow powder.

Yield 0.59 g (8%) of (2-hydroxy-5-methoxyphenyl)-(4-hydroxyphenyl)-methanone M.p. 144.5–147.5° C. (ethyl acetate/petrol). $^1$H-NMR (CDCl$_3$, 300 MHz) δ: 3.74 (s, 3H), 6.30 (bs, 1H), 6.92 (dm, 2H), 7.01 (d, 1H), 7.10 (d, 1H), 7.13 (dd, 1H), 7.68 (dm, 2H), 11.50 (s, 1H). LRMS (El) 244 (M$^+$), 150 (M-PhOH).

Step 3:

4-(4-Acetoxyphenyl)-3-phenyl-6-methoxy-coumarin

A mixture of (2-hydroxy-5-methoxyphenyl)-(4-hydroxyphenyl)-methanone (0.59 g, 2.42 mmol), acetic anhydride (1.15 ml, 12.1 mmol), triethylamine (0.44 ml, 3.16 mmol), and phenyl acetic acid (0.33 g, 2.42 mmol) was stirred at 135° C. for 18 h. The resulting orange coloured solution was poured into water (20 ml) and stirred for 3 h, and the resulting mixture of aqueous solution plus sticky solid was diluted with ethyl acetate (20 ml) to dissolve the solid, and the organic layer separated. The aqueous phase was further extracted with ethyl acetate (2×20 ml). The combined organic extracts were washed with water, then brine, dried over sodium sulfate and evaporated to give a yellow/orange gum. This gum was dissolved in a minimum of ether and petrol added to precipitate the title compound as an off white powder.

Yield 0.49 g (52%) of 4-(4-acetoxyphenyl)-3-phenyl-6-methoxy-coumarin. $^1$H-NMR (CDCl$_3$, 300 MHz) δ: 2.28 (s, 3H), 3.72 (s, 3H), 6.70 (d, 1H), 7.04–7.25 (m, 1OH), 7.48 (d, 1H). LRMS (El) 386 (M$^+$), 344, 327, 316, 43.

Step 4:

(±)-cis-6-Methoxy-3-phenyl-4-(4-(2-pyrrolidinoethoxy)phenyl)chromane

Lithium aluminium hydride (0.96 g, 2.54 mmol) was added in small portions to a stirred solution of 4-(4-acetoxyphenyl)-3-phenyl-6-methoxy-coumarin (0.49 g, 1.27 mmol) in tetrahydrofuran (75 ml). The resulting mixture was stirred for 30 min., 6M hydrochloric acid (4 ml) added dropwise, and the mixture heated to 65° C. for 3 h. The mixture was cooled to room temperature, diluted with 100 ml water, and the product extracted into ethyl acetate (2×100 ml). The extracts were washed with brine, dried over sodium sulfate and evaporated to give a yellow gum. This gum was dissolved in ethanol (100 ml), and palladium on carbon (5%, 0.045 g, 0.02 mmol) added, then the mixture was hydrogenated for 18 h. The catalyst was removed by filtration and the solvents evaporated to give an orange gum, which was vacuum dried. The gum was dissolved in dry acetone (20 ml) then potassium carbonate (1.87 g, 13.50 mmol), 1-(2-chloroethyl)pyrrolidine hydrochloride (0.257 g, 1.51 mmol) and sodium iodide (0.01 g, catalyst) were added and the mixture heated to 60° C. for 20 h. The inorganic solids were removed by filtration and the solvent removed to give an orange gum, which was purified by column chromatography on silica gel 60 with 9:1 dichloromethane/methanol eluent. This gave the product as a pale orange gum, which was vacuum dried.

Yield 0.34 g (62%) of (±)-cis-6-methoxy-3-phenyl-4-(4-(2-pyrrolidinoethoxy)phenyl)chromane. $^1$H-NMR (CDCl$_3$, 300 MHz) δ: 1.70–1.90 (m, 4H), 2.55–2.70 (m, 4H), 2.85 (t, 2H), 3.56 (ddd, 1H), 3.69 (s, 3H), 4.02 (t, 2H), 4.15–4.28 (m, 2H), 4.40 (dd, 1H), 6.45–6.55 (m, 3H), 6.55–6.72 (m, 4H), 6.79 (dd, 1H), 6.90 (d, 1H), 7.10–7.20 (m, 3H).

Step 5:
(±)-cis-6-Hydroxy-3-phenyl-4-(4-(2-pyrrolidinoethoxy) phenyl)chromane

A mixture of (±)-cis-6-methoxy-3-phenyl4-(4-(2-pyrrolidinoethoxy)phenyl)chromane (0.34 g, 0.79 mmol) and pyridine hydrochloride (0.91 g, 7.9 mmol) was stirred at 135° C. for 18 h, cooled to room temperature and the resulting dark solid dissolved in a mixture of methanol (10 ml), water (50 ml) and dichloromethane (50 ml). The aqueous layer was separated and further extracted with 4:1 dichloromethane/methanol (50 ml). The organic layers were combined, washed with brine, dried over magnesium sulfate, and evaporated. The product was purified by column chromatography on silica gel 60, with 5% methanol in dichloromethane as eluent. The resulting gum was dissolved in approximately 1 ml ethanol and then diethylether added. This resulted in the precipitation of the title compound as a partial hydrochloride salt. The solid was dissolved in dichloromethane, washed with sodium hydrogen carbonate solution, brine, dried over magnesium sulfate and evaporated to give the title compound as a pale yellow foam.

Yield 70 mg (21%) of (±)-cis-6-hydroxy-3-phenyl-4-(4-(2-pyrrolidinoethoxy)phenyl)chromane. $^1$H-NMR (CDCl$_3$, 200 MHz) δ: 1.70–1.90 (m, 4H), 2.55–2.75 (m, 4H), 2.85 (t, 2H), 3.55 (ddd, 1H), 3.90–4.10 (m, 2H), 4.15–4.28 (m, 2H), 4.40 (dd, 1H), 6.38 (d, 1H), 6.42–6.60 (m, 4H), 6.60–6.75 (m, 3H), 6.85 (d, 1H), 7.05–7.25 (m, 3H), phenol OH not observed.

EXAMPLE 2

(±)-cis-6-Hydroxy-3-(3-hydroxyphenyl)-4-(4-(2-pyrrolidinoethoxy)phenyl)chromane

The title compound was prepared in a manner exactly analogous to that described for Example 1, with the substitution of 3-methoxyphenyl acetic acid in the place of phenyl acetic acid in Step 3.

Thus, (±)-cis-6-methoxy-3-(3-methoxyphenyl)-4-(4-(2-pyrrolidinoethoxy)phenyl)-chromane (0.24 g, 0.52 mmol) was de-methylated by heating with pyridine hydrochloride (0.60 g, 5.20 mmol) to give the title compound, after purification and drying, as a colourless gum.

Yield 95 mg (35%) of (±)-cis-6-hydroxy-3-(3-hydroxyphenyl)-4-(4-(2-pyrrolidinoethoxy)phenyl) chromane. $^1$H-NMR (MeOH-d$_4$, 200 MHz) δ: 1.90–2.10 (m, 4H), 3.05–3.25 (m, 4H), 3.25–3.55 (m, 3H), 4.10–4.42 (m, 5H), 6.15 (m, 1H), 6.26 (dm,1H), 6.30 (d, 1H), 6.50–6.80 (m, 7H), 6.92 (dd, 1H), phenol OH signals not observed.

We claim:

1. A compound of the formula I in which substituents R$^2$ and R$^3$ are arranged in cis-configuration:

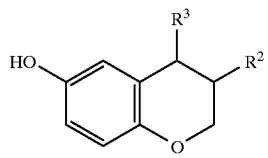

(I)

wherein:

R$^2$ is phenyl optionally substituted with 1 to 5 substituents independently selected from the group consisting of OH, halogen, nitro, cyano, SH, SR$^4$, trihalo-C$_1$–C$_6$-alkyl, C$_1$–C$_6$-alkyl, C$_1$–C$_6$-alkoxy and phenyl;

R$^3$ is:
(a) phenyl substituted with —X—(CH$_2$)$_n$—Y, wherein:
X is a valency bond, O or S,
n is an integer in the range of 1 to 12,
Y is a pyrrolidine ring optionally substituted with 1 to 3 substituents independently selected from the group consisting of H, OH, halogen, nitro, cyano, SH, SR$^4$, trihalo-C$_1$–C$_6$-alkyl, C$_1$–C$_6$-alkyl and C$_1$–C$_6$-alkoxy; or
(b) —(CH$_2$)$_n$—Y, wherein n and Y are as defined above and R$^4$ is C$_1$–C$_6$-alkyl;

or an optical or a geometrical isomer, a pharmaceutically acceptable ester, or ether or a salt thereof.

2. A compound of the formula I in which substituents R$^2$ and R$^3$ are arranged in cis-configuration:

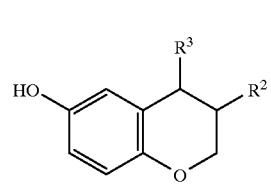

(I)

wherein:

R$^2$ is phenyl optionally substituted with 1 to 3 substituents independently selected from the group consisting of OH, halogen, nitro, cyano, SH, SR$^4$, trihalo-C$_1$–C$_6$-alkyl, C$_1$–C$_6$-alkyl and C$_1$–C$_6$-alkoxy;

R$^3$ is:
(a) phenyl substituted with —X—(CH$_2$)$_n$—Y, wherein:
X is a valency bond, O or S,
n is an integer in the range of 1 to 12,
Y is a pyrrolidine ring optionally substituted with 1 to 3 substituents independently selected from the group consisting of H, OH, halogen, nitro, cyano, SH, SR$^4$, trihalo-C$_1$–C$_6$-alkyl, C$_1$–C$_6$-alkyl and C$_1$–C$_6$-alkoxy; or
(b) —(CH$_2$)$_n$—Y, wherein n and Y are as defined in claim 1; and R$^4$ is C$_1$–C$_6$-alkyl; or an optical or a geometrical isomer, a pharmaceutically acceptable ester, or ether or a salt thereof.

3. A compound according to claims 1 in which R$^2$ is phenyl optionally substituted with 1 to 5 substituents independently selected from the group consisting of OH, halogen, nitro, cyano, SH, SR$^4$, trihalo-C$_1$–C$_6$-alkyl, C$_1$–C$_6$-alkyl and C$_1$–C$_6$-alkoxy.

4. A compound according to claims 1 in which R$^2$ is phenyl optionally substituted with 1 to 3 substituents independently selected from the group consisting of OH, halogen, nitro, cyano, SH, SR$^4$, trihalo-C$_1$–C$_6$-alkyl, C$_1$–C$_6$-alkyl and C$_1$–C$_6$-alkoxy.

5. A compound according to claim 1 In which R$^3$ is phenyl substituted with —X—(CH$_2$)$_n$—Y, wherein:

X is valency bond, O or S, n is an integer In the range of 1 to 12,

Y is a pyrrolidine ring optionally substituted with 1 to 3 substituents independently selected from the group consisting of H, OH, halogen, nitro, cyano, SH, SR$^4$, trihalo-C$_1$–C$_6$-alkyl, C$_1$–C$_6$-alkyl and C$_1$–C$_6$-alkoxy.

6. A compound according to claim 1 wherein R$^3$ is —(CH$_2$)$_n$—Y, wherein n and Y are as defined above.

7. A compound according to claim 1 having the formula

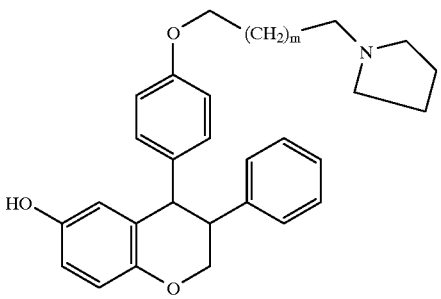

wherein m is an integer from 0 to 10.

8. A compound according to claim 1 having the formula

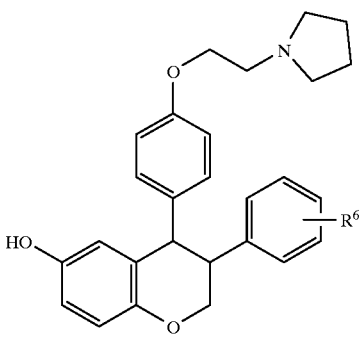

wherein R⁶ represents one or more of the following substituents: methoxy, hydroxy, trifluormethyl, fluoro or chloro.

9. A compound according to claim 1 selected from the following:

(−)-cis-6-Hydroxy-3-phenyl-4-(4-(2-pyrrolidinoethoxy)phenyl)chromane,
(−)-cis-6-Hydroxy-3-phenyl-4-(4-(3-pyrrolidinopropoxy)phenyl)chromane,
(−)-cis-6-Hydroxy-3-phenyl-4-(4-(4-pyrrolidinobutoxy)phenyl)chromane,
(−)-cis-6-Hydroxy-3-phenyl-4-(4-(5-pyrrolidinopentoxy)phenyl)chromane,
(−)-cis-6-Hydroxy-3-phenyl-4-(4-(6-pyrrolidinohexyloxy)phenyl)chromane,
(−)-cis-6-Hydroxy-3-phenyl-4-(4-(7-pyrrolidinoheptyloxy)phenyl)chromane,
(−)-cis-6-Hydroxy-3-phenyl-4-(4-(8-pyrrolidinooctyloxy)phenyl)chromane,
(−)-cis-6-Hydroxy-3-phenyl-4-(4-(9-pyrrolidinononyloxy)phenyl)chromane,
(−)-cis-6-Hydroxy-3-phenyl-4-(4-(10-pyrrolidinodecyloxy)phenyl)chromane,
(−)-cis-6-Hydroxy-3-phenyl-4-(4-(11-pyrrolidinoundecyloxy)phenyl)chromane,
(−)-cis-6-Hydroxy-3-phenyl-4-(4-(12-pyrrolidinododecyloxy)phenyl)chromane,
(−)-cis-6-Hydroxy-3-(4-hydroxyphenyl)-4-(4-(2-pyrrolidinoethoxy)phenyl)chromane,
(−)-cis-6-Hydroxy-3-(4-trifluoromethylphenyl)-4-(4-(2-pyrrolidinoethoxy)phenyl)chromane,
(−)-cis-6-Hydroxy-3-(4-fluorophenyl)-4-(4-(2-pyrrolidinoethoxy)phenyl)chromane,
(−)-cis-3-(4-Chlorophenyl)-6-hydroxy-4-(4-(2-pyrrolidinoethoxy)phenyl)chromane,
(−)-cis-3-(3,4-Dimethoxyphenyl)-6-hydroxy-4-(4-(2-pyrrolidinoethoxy)phenyl)chromane,
(−)-cis-6-Hydroxy-3-(pentafluorophenyl)-4-(4-(2-pyrrolidinoethoxy)phenyl)chromane,
(+)-cis-6-Hydroxy-3-phenyl-4-(4-(2-pyrrolidinoethoxy)phenyl)chromane,
(+)-cis-6-Hydroxy-3-phenyl-4-(4-(3-pyrrolidinopropoxy)phenyl)chromane,
(+)-cis-6-Hydroxy-3-phenyl-4-(4-(4-pyrrolidinobutoxy)phenyl)chromane,
(+)-cis-6-Hydroxy-3-phenyl-4-(4-(5-pyrrolidinopentoxy)phenyl)chromane,
(+)-cis-6-Hydroxy-3-phenyl-4-(4-(6-pyrrolidinohexyloxy)phenyl)chromane,
(+)-cis-6-Hydroxy-3-phenyl-4-(4-(7-pyrrolidinoheptyloxy)phenyl)chromane,
(+)-cis-6-Hydroxy-3-phenyl-4-(4-(8-pyrrolidinooctyloxy)phenyl)chromane,
(+)-cis-6-Hydroxy-3-phenyl-4-(4-(9-pyrrolidinononyloxy)phenyl)chromane,
(+)-cis-6-Hydroxy-3-phenyl-4-(4-(10-pyrrolidinodecyloxy)phenyl)chromane,
(+)-cis-6-Hydroxy-3-phenyl-4-(4-(11-pyrrolidinoundecyloxy)phenyl)chromane,
(+)-cis-6-Hydroxy-3-phenyl-4-(4-(12-pyrrolidinododecyloxy)phenyl)chromane,
(+)-cis-6-Hydroxy-3-(4-hydroxyphenyl)-4-(4-(2-pyrrolidinoethoxy)phenyl)chromane,
(+)-cis-6-Hydroxy-3-(4-trifluoromethylphenyl)-4-(4-(2-pyrrolidinoethoxy)phenyl)chromane,
(+)-cis-6-Hydroxy-3-(4-fluorophenyl)-4-(4-(2-pyrrolidinoethoxy)phenyl)chromane,
(+)-cis-3-(4-Chlorophenyl)-6-hydroxy-4-(4-(2-pyrrolidinoethoxy)phenyl)chromane,
(+)-cis-3-(3,4-Dimethoxyphenyl)-6-hydroxy4-(4-(2-pyrrolidinoethoxy)phenyl)chromane, and
(+)-cis-6-Hydroxy-3-(pentafluorophenyl)-4-(4-(2-pyrrolidinoethoxy)phenyl)chromane, or any mixture thereof.

10. A compound according to claim 1 selected from the following:

(±)-cis-6-Hydroxy-3-phenyl-4-(4-(2-pyrrolidinoethoxy)phenyl)-chromane, and
(±)-cis-6-Hydroxy-3-(3-hydroxyphenyl)-4-(4-(2-pyrrolidinoethoxy)phenyl)chromane, or pure enantiomer thereof.

11. A pharmaceutical composition comprising an effective amount of a compound according to claim 1 a pharmaceutical acceptable salt thereof and a pharmaceutical carrier or diluent.

12. A pharmaceutical composition according to claim 11 in the form of an oral dosage unit or parenteral dosage unit.

13. A method of treating estrogen related diseases or syndromes caused by an estrogen-deficient state in a mammal, comprising administering to a subject in need thereof an effective amount of a compound according to claim 1.

14. A method for treating or preventing bone loss or osteoporosis comprising administering to a mammal in need thereof an effective amount of a compound of claim 1.

15. A method for treating cardiovascular diseases, cognitive disorders, menopausal symptoms, incontinence, obesity, dysmenorrhea, dysfunctional uterine bleeding, acne, hirsutism, post-partum lactation, threatened or habitual abortion estrogen-dependent cancers, senile dementia-Alzheimer's type, prostatic carcinoma for regulating glucose metabolism, and for aiding ovarian development, said method comprising administering to a mammal in need thereof an effective amount of a compound of claim 1.

16. The method of claim 15, wherein the menopausal symptoms are flushing, urogenital atrophy, depression, mania, or schizophrenia.

* * * * *

UNITED STATES PATENT AND TRADEMARK OFFICE
CERTIFICATE OF CORRECTION

PATENT NO. : 5,958,967
DATED :
INVENTOR(S) : September 28, 1999
Jacobsen et al.

It is certified that error appears in the above-identified patent and that said Letters Patent is hereby corrected as shown below:

Col. 24, line 57, claim 5    change "In" to -- in --

Signed and Sealed this

Twenty-sixth Day of September, 2000

Attest:

Q. TODD DICKINSON

Attesting Officer    Director of Patents and Trademarks